(12) United States Patent
Miller et al.

(10) Patent No.: US 7,658,768 B2
(45) Date of Patent: *Feb. 9, 2010

(54) BONE GRAFT SUBSTITUTE COMPOSITION

(75) Inventors: Leasa C. Miller, Covington, TN (US); Kelly Coupe Richelsoph, Memphis, TN (US); Jon P. Moseley, Arlington, TN (US)

(73) Assignee: Wright Medical Technology, Inc., Arlington, TX (US)

(*) Notice: Subject to any disclaimer, the term of this patent is extended or adjusted under 35 U.S.C. 154(b) by 281 days.

This patent is subject to a terminal disclaimer.

(21) Appl. No.: 11/872,564

(22) Filed: Oct. 15, 2007

(65) Prior Publication Data

US 2008/0031917 A1    Feb. 7, 2008

Related U.S. Application Data

(63) Continuation of application No. 10/448,885, filed on May 30, 2003, now Pat. No. 7,291,179, which is a continuation-in-part of application No. 10/179,533, filed on Jun. 24, 2002, now Pat. No. 6,652,887.

(51) Int. Cl.
*A61K 31/32* (2006.01)
*A61F 2/28* (2006.01)

(52) U.S. Cl. ............. 623/23.63; 623/23.51; 623/23.61; 623/16.11; 424/549; 424/682; 424/696

(58) Field of Classification Search .................. None
See application file for complete search history.

(56) References Cited

U.S. PATENT DOCUMENTS

| | | | |
|---|---|---|---|
| 3,813,312 A | 5/1974 | Kinkade et al. | |
| 4,430,760 A | 2/1984 | Smestad | |
| 4,568,536 A | 2/1986 | Kronenthal et al. | |
| 4,595,713 A | 6/1986 | St. John | |
| 4,596,574 A | 6/1986 | Urist | |
| 4,612,009 A | 9/1986 | Drobnik et al. | |
| 4,619,655 A | 10/1986 | Hanker et al. | |
| 4,650,665 A | 3/1987 | Kronenthal et al. | |
| 4,681,763 A | 7/1987 | Nathanson et al. | |
| 4,820,306 A | 4/1989 | Gorman et al. | |
| 4,880,660 A | 11/1989 | Aasen et al. | |
| 4,882,149 A | 11/1989 | Spector | |
| 4,892,734 A | 1/1990 | Leonard | |
| 4,975,526 A | 12/1990 | Kuberasampath et al. | |
| 4,994,030 A | 2/1991 | Glowczewskie, Jr. et al. | |
| 5,061,286 A | 10/1991 | Lyle | |
| 5,073,373 A | 12/1991 | O'Leary et al. | |
| 5,147,403 A | 9/1992 | Gitelis | |
| 5,162,114 A | 11/1992 | Kuberasampath et al. | |
| 5,219,897 A | 6/1993 | Murray | |
| 5,236,456 A | 8/1993 | O'Leary et al. | |
| 5,236,971 A | 8/1993 | Murray | |
| 5,264,214 A | 11/1993 | Rhee et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,306,304 A | 4/1994 | Gendler | |
| 5,314,476 A | 5/1994 | Prewett et al. | |
| 5,320,844 A | 6/1994 | Liu | |
| 5,336,699 A | 8/1994 | Cooke et al. | |
| 5,356,629 A | 10/1994 | Sander et al. | |
| 5,366,507 A | 11/1994 | Sottosanti | |
| 5,385,887 A | 1/1995 | Yim et al. | |
| 5,405,390 A | 4/1995 | O'Leary et al. | |
| 5,417,975 A | 5/1995 | Lussi et al. | |
| 5,425,769 A | 6/1995 | Snyders et al. | |
| 5,439,684 A | 8/1995 | Prewett et al. | |
| 5,462,722 A | 10/1995 | Liu et al. | |
| 5,482,551 A | 1/1996 | Morris et al. | |
| 5,484,601 A | 1/1996 | O'Leary et al. | |
| 5,507,813 A | 4/1996 | Dowd et al. | |
| 5,510,396 A | 4/1996 | Prewett et al. | |
| 5,512,610 A | 4/1996 | Lin | |
| 5,531,791 A | 7/1996 | Wolfinbarger, Jr. | |

(Continued)

FOREIGN PATENT DOCUMENTS

DE    196 20 117 C1    7/1997

(Continued)

OTHER PUBLICATIONS

Girardi et al, "The Effect of Bone Graft Extenders to Enhance the Performance of Iliac Crest Bone Grafts in Instrumented Lumbar Spine Fusion." Orthopedics, May 2003, vol. 26, No. 5 Supplement, pp. s545-s548.*

(Continued)

*Primary Examiner*—Allison M Ford
(74) *Attorney, Agent, or Firm*—Alston & Bird LLP

(57) ABSTRACT

Bone graft substitute compositions and methods of making the compositions are disclosed. In some embodiments, a method of making a composition includes contacting a mixing solution with a first mixture having calcium sulfate hemihydrate and a plasticizing material to form a second mixture; waiting a predetermined period of time after forming said second mixture; and then contacting demineralized bone with the second mixture to form the composition. A composition can be formed from a kit including a first mixture having calcium sulfate hemihydrate and a plasticizing substance, a second mixture having demineralized bone, and a mixing solution. The first and second mixtures and the mixing solution are unblended.

24 Claims, No Drawings

U.S. PATENT DOCUMENTS

| | | | |
|---|---|---|---|
| 5,569,308 | A | 10/1996 | Sottosanti |
| 5,573,771 | A | 11/1996 | Geistich et al. |
| 5,578,662 | A | 11/1996 | Bennett et al. |
| 5,614,206 | A | 3/1997 | Randolph et al. |
| 5,618,549 | A | 4/1997 | Patat et al. |
| 5,676,146 | A | 10/1997 | Scarborough |
| 5,681,873 | A | 10/1997 | Norton et al. |
| 5,697,981 | A | 12/1997 | Ison et al. |
| 5,700,289 | A | 12/1997 | Breitbart et al. |
| 5,707,962 | A | 1/1998 | Chen et al. |
| 5,727,945 | A | 3/1998 | Dannenbaum |
| 5,756,127 | A | 5/1998 | Grisoni et al. |
| 5,763,416 | A | 6/1998 | Bonadio et al. |
| 5,766,618 | A | 6/1998 | Laurencin et al. |
| 5,769,897 | A | 6/1998 | Harte |
| 5,788,976 | A | 8/1998 | Bradford |
| 5,807,567 | A | 9/1998 | Randolph et al. |
| 5,824,087 | A | 10/1998 | Aspden et al. |
| 5,830,493 | A | 11/1998 | Yokota et al. |
| 5,861,445 | A | 1/1999 | Xu et al. |
| 5,899,939 | A | 5/1999 | Boyce et al. |
| 5,910,315 | A | 6/1999 | Stevenson et al. |
| 5,948,426 | A | 9/1999 | Jefferies |
| 5,948,428 | A | 9/1999 | Lee et al. |
| 5,964,805 | A | 10/1999 | Stone |
| 5,972,368 | A | 10/1999 | McKay |
| 5,981,828 | A | 11/1999 | Nelson et al. |
| 6,030,635 | A | 2/2000 | Gertzman et al. |
| 6,030,636 | A | 2/2000 | Randolph et al. |
| 6,037,519 | A | 3/2000 | McKay |
| 6,051,247 | A | 4/2000 | Hench et al. |
| 6,056,970 | A | 5/2000 | Greenawalt et al. |
| 6,071,530 | A | 6/2000 | Polson et al. |
| 6,083,522 | A | 7/2000 | Chu et al. |
| 6,118,043 | A | 9/2000 | Nies et al. |
| 6,224,635 | B1 | 5/2001 | Ricci et al. |
| 6,340,477 | B1 | 1/2002 | Anderson |
| 6,409,823 | B1 | 6/2002 | Shake et al. |
| 6,478,825 | B1 | 11/2002 | Winterbottom et al. |
| 6,652,887 | B1 | 11/2003 | Richelsoph et al. |
| 6,770,695 | B2 | 8/2004 | Ricci et al. |
| 7,163,691 | B2 | 1/2007 | Knaack et al. |
| 7,211,266 | B2 | 5/2007 | Cole et al |
| 2002/0071827 | A1 | 6/2002 | Petersen et al. |
| 2002/0110541 | A1 | 8/2002 | Petersen |
| 2003/0050710 | A1 | 3/2003 | Petersen et al. |
| 2003/0235621 | A1 | 12/2003 | Miller et al. |

FOREIGN PATENT DOCUMENTS

| | | |
|---|---|---|
| GB | 2 093 348 A | 9/1982 |
| WO | WO 89/04646 A1 | 6/1989 |
| WO | WO 91/00252 A1 | 1/1991 |
| WO | WO 96/39203 A1 | 12/1996 |
| WO | WO 98/40113 A1 | 9/1998 |
| WO | WO 99/15150 A1 | 4/1999 |
| WO | WO 00/74690 A1 | 12/2000 |
| WO | WO 02/05750 A2 | 1/2002 |
| WO | WO 03/024316 A2 | 3/2003 |
| WO | WO 03/030956 A2 | 4/2003 |
| WO | WO 03/045455 A1 | 6/2003 |

OTHER PUBLICATIONS

Wilkins et al, "Percutaneous Treatment of Long Bone Nonunions: The Use of Autologous Bone Marrow and Allograft Bone Matrix." Orthopedics, May 2003, vol. 26, No. 5 supplement, pp. s549-s554.*
Jones et al, "Interpositional Arthroplasty (Jones Technique) for the Treatment of Herniated Lumbar Disks: A Modification of the Soft Posterior Lumbar Interbody Fusion" Orthopedics, May 2003, vol. 26, No. 5, Supplement, pp. s555-s559.*
Rodgers, W.B. "Bone Marrow Aspiration" Orthopedics, May 2003, vol. 26, No. 5 Supplement, pp. s560.*
Turner et al, "Restoration of Large Bone Defects Using a Hard-Setting, Injectable Putty Containing Demineralized Bone Particles Compared to Cancellous Autograft Bone." Orthopedics, May 2003, vol. 26, No. 5, supplement, pp. s561-s565.*
Wilkins et al, "The Effect of AlloMatrix Injectable Putty on the Outcome of Long Bone Applications" Orthopedics, May 2003, vol. 26, No. 5 Supplement, pp. s567-s570.*
Turner et al, "Osseous Healing Using Injectable Calcium Sulfate-Based Putty for the Delivery of Demineralized Bone Matrix and Cancellous Bone Chips" Orthopedics, May 2003, vol. 26, No. 5 supplement, pp. s571-s575.*
Turner et al, "Resorption Evaluation of a Large Bolus of Calcium Sulfate in a Canine Medullary Defect" Orthopedics, May 2003, vol. 26, No. 5, supplement, pp. s577-s579.*
Urban et al, "Healing of Large Defects Treated With Calcium Sulfate Pellets Containing Demineralized Bone Matrix Particles" Orthopedics, May 2003, vol. 26, No. 5, supplement, pp. s581-s585.*
Neel, M. "The Use of a Periosteal Replacement Membrane for Bone Graft Containment at Allograft-Host Junctions After Tumor Resection and Reconstruction With Bulk Allograft." Orthopedics, May 2003, vol. 26, No. 5, supplement, pp. s587-s589.*
Beniker et al, "The Use of Acellular Dermal Matrix as a Scaffold for Periosteum Replacement" Orthopedics, May 2003, vol. 26, No. 5, supplement. pp. s591-s596.*
Adkisson et al., "Rapid Quantitative Bioassay of Osteoinduction", *Journal of Orthopaedic Research*, 18:503-511, 2000.
Anson, D., "Saving Periodontally 'Hopeless Teeth' Using Calcium Sulfate and Demineralized Freeze-Dried Bone Allograft", *Compendium*, 1998, pp. 284-298, vol. 19, No. 3.
Betz, Randal R., M.D., "Limitations of Autograft and Allograft: New Synthetic Solutions", *Orthopedics*, vol. 25, No. 5, Supplement May 2002, pp. s561-s570.
Biomaterial Tutorial, www.btec.cmu.edu/tutorial/biomaterials/biomaterials.htm, undated.
"Bone Graft Substitutes Safe, Effective", *AMA Science News Media Briefings*, Dec. 6, 2001, (2 pages).
Greenwald et al., "Bone-Graft Substitutes: Facts, Fictions, and Applications", *The Journal of Bone & Joint Surgery*, vol. 83-A, Supplement 2, Part 2, 2001, pp. 98-103.
Grimandi et al., "In vitro evaluation of a new injectable calcium phosphate material", *J. Biomed. Mater Res.*, 1998, pp. 660-666, vol. 39, John Wiley & Sons.
Hanker et al., "Setting of Composite Hydroxylapatite/Plaster Implants with Blood for Bone Reconstruction", Proceedings of the 44th Annual Meeting of the Electron Microscopy Society of America, 1986, pp. 328-329.
Kelly, Evelyn B., Ph.D., "New Frontiers in Bone Grafting", *Orthopaedic Technology Review*, vol. 2, No. 9, Oct. 2000, (8 pages).
Turner et al., "Radiographic and Histologic Assessment of Calcium Sulfate in Experimental Animal Models and Clinical use as a Resorbable Bone-Graft Substitute, A Bone-Graft Expander, and a Method for Local Antibiotic Delivery", *The Journal of Bone and Joint Surgery*, vol. 83-A, Supp. 2, Part 1, 2001, pp 8-18.

\* cited by examiner

BONE GRAFT SUBSTITUTE COMPOSITION

CROSS-REFERENCE TO RELATED APPLICATIONS

This application is a continuation application of U.S. application Ser. No. 10/448,885, filed May 30, 2003 now U.S. Pat. No. 7,291,179, which is a continuation-in-part application of U.S. application Ser. No. 10/179,533, filed Jun. 24, 2002 now U.S. Pat. No. 6,652,887, which are hereby incorporated herein in their entirety by reference.

TECHNICAL FIELD

The invention relates to bone graft substitute compositions.

BACKGROUND OF THE INVENTION

Compositions containing calcium sulfate can be used as filler for voids and/or defects defined by bone. In some embodiments, the compositions can promote bone growth.

BRIEF SUMMARY OF THE INVENTION

In one aspect, the invention relates to bone graft substitute compositions.

In another aspect, the invention features a method of making a composition. The method includes contacting a mixing solution with a first mixture having calcium sulfate hemihydrate and a plasticizing material to form a second mixture; and after waiting a predetermined time, contacting demineralized bone with the second mixture to form the composition.

In another aspect, the invention features a kit, including a first mixture having calcium sulfate hemihydrate and a plasticizing substance, a second mixture having demineralized bone, the second mixture being unblended with the first mixture, and a mixing solution unblended with the first and second mixtures. The kit can include instructions for making a bone graft composition as described herein.

The first mixture can further include a first material capable of accelerating formation of calcium sulfate dihydrate from the calcium sulfate hemihydrate, such as calcium sulfate dihydrate coated with sucrose.

Other aspects, features, and advantages of the invention will be apparent from the description of the preferred embodiments thereof and from the claims.

DETAILED DESCRIPTION OF THE INVENTION

Bone graft substitute compositions including surgical-grade calcium sulfate hemihydrate (CaSO$_4$·½H$_2$O); demineralized bone matrix; a material that accelerates hardening of the composition ("an accelerant"); a plasticizing material; and a mixing solution are described in Applicants' co-pending U.S. Ser. No. 10/179,533. Furthermore, bone graft compositions including surgical-grade calcium sulfate hemihydrate (CaSO$_4$·½H$_2$O); demineralized bone matrix; a plasticizing material; and a mixing solution are also described in Applicants'0 co-pending U.S. Ser. No. 10/060,697 (and other members of that family). These compositions are prepared by mixing all the dry materials together simultaneously, and then combining the dry materials with the mixing solution.

Here, Applicants have found that during use, if the components are mixed together in a predetermined order and timing, consistent results, such as repeatable set times, are much likely to be obtained. Applicants have found that the order and timing to be to first form a first mixture including the calcium sulfate, the plasticizing material, and the optional accelerant in a container. The mixing solution is then added to the container. The first mixture and the solution are mixed until blended, e.g., for about thirty seconds, and allowed to sit, e.g., for about another thirty seconds. During the initial one minute, the blend of the first mixture and mixing solution can be mixed the entire time or only a portion of the time (e.g., mixing and sitting).

After a total of about one minute, the demineralized bone is then added to the blend and mixed thoroughly to form the composition. The composition can be delivered to a target site (e.g., a void or a defect) by injecting the composition through a syringe, and/or by forming (e.g., molding) a paste or a putty of the composition and applying the composition by hand (e.g., using fingers). After about 5-10 minutes, the composition can harden ex vivo or in vivo, e.g., to a hardness sufficient to support orthopedic hardware.

Without wishing to be bound by theory, it is believed that during use, e.g., after mixing the mixture of powders with the mixing solution, the calcium sulfate hemihydrate is converted, e.g., changes crystalline form, into calcium sulfate dihydrate (CaSO$_4$·2H$_2$O), which hardens the composition. Calcium sulfate dihydrate is capable of being sorbed by the body. It is believed that the method described above of making the composition allows the calcium sulfate hemihydrate to begin converting to calcium sulfate dihydrate before other ingredients of the composition, such as proteins from the demineralized bone, interfere (e.g., stop) the conversion. In any event, beneficial results have been found by waiting a predetermined period of time before adding the demineralized bone to the second mixture. This method is different from, for example, U.S. Pat. No. 5,385,887, to Yim, in which calcium sulfate is added directly to a blood-BMP mixture.

For purposes of describing the concentrations of materials in the bone graft substitute composition, the composition includes 100 parts of calcium sulfate, e.g., calcium sulfate hemihydrate. Methods of making a calcium sulfate hemihydrate are described in U.S. Pat. Nos. 5,614,206, 5,807,567, and 6,030,636, each of which is hereby incorporated by reference in its entirety.

The demineralized bone matrix is believed to enhance bone growth. In some embodiments, the demineralized bone matrix is freeze-dried to less than about 6% moisture. The demineralized bone matrix can have a particle size of about 125-850 microns, e.g., about 125-710 microns. The particle size can be greater than or equal to about 125, 150, 200, 250, 300, 350, 400, 450, 500, 550, 600, 650, 700, 750, or 800 microns; and/or less than or equal to about 850, 800, 750, 700, 650, 600, 550, 500, 450, 400, 350, 300, 250, 200, or 150 microns. The calcium content in the demineralized bone matrix can be about less than eight (8) percent. Demineralized bone matrix is available, e.g., from Allosource (Denver, Colo.) or DCI (Nashville, Tenn.).

For 100 parts of calcium sulfate (e.g., CaSO$_4$·½H$_2$O), the composition includes between about 10 and about 30 parts of demineralized bone matrix, such as between about 15 and about 25 parts, or between about 19 and about 21 parts, or about 20 parts. In embodiments, the composition may include greater than or equal to about 10, 12, 14, 16, 18, 20, 22, 24, 26, or 28 parts of demineralized bone matrix; and/or less than or equal to about 30, 28, 26, 24, 22, 20, 18, 16, 14, or 12 parts of demineralized bone matrix.

As described in Applicants' co-pending U.S. Ser. No. 10/179,533 and without wishing to be bound by theory, the accelerant is believed to enhance, e.g., accelerate, the conversion of calcium sulfate hemihydrate to calcium sulfate dihydrate. In particular, it is believed that particles of the accelerant act as crystallization nucleation sites for the conversion of calcium sulfate hemihydrate to calcium sulfate dihydrate. Examples of accelerants include calcium sulfate dihydrate, potassium sulfate, or sodium sulfate. Other examples include ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, hereby incorporated by reference in its entirety.

For 100 parts of calcium sulfate (e.g., $CaSO_4 \cdot \frac{1}{2}H_2O$), the composition includes between about 0.5 and about 5 parts of the accelerant, such as about 4.8 parts, or between about 1 and about 4 parts, or between about 2.5 and about 3.5 parts, or about 3 parts. The composition may include greater than or equal to about 0.5, 1, 1.5, 2, 2.5, 3, 3.5, 4, or 4.5 parts of the accelerant; and/or less than or equal to about 5, 4.5, 4, 3.5, 3, 2.5, 2, 1.5, or 1 parts of the accelerant. Mixtures of two or more accelerants can be used.

The plasticizing material is believed to provide the bone graft substitute composition with a consistency that helps the composition to form into a paste or putty, or to flow, e.g., to be injectable. Examples of plasticizing materials include cellulose derivatives, such as sodium carboxymethylcellulose, methylcellulose (MC), hydroxypropylmethylcellulose (HPMC), hydroxypropylcellulose (HPC), ethylcellulose (EC), hydroxyethylcellulose or cellulose acetate butyrate. Other examples of plasticizing material include high molecular weight alcohols including glycerol and vinyl alcohols, stearic acid, and hyaluronic acid.

For 100 parts of calcium sulfate (e.g., $CaSO_4 \cdot \frac{1}{2}H_2O$), the composition includes between about 0.5 and about 5 parts of the plasticizing material, such as between about 1 and about 3 parts, or between about 1.5 and about 2.5 parts, or about 2 parts. The composition may include greater than or equal to about 0.5, 1, 1.5, 2, 2.5, 3, 3.5, 4, or 4.5 parts of the plasticizing material; and/or less than or equal to about 5, 4.5, 4, 3.5, 3, 2.5, 2, 1.5, or 1 parts of the plasticizing material. Mixtures of two or more plasticizing materials can be used.

The mixing solution is generally selected to provide the composition with a desired consistency and hardening time. Examples of a mixing solution include water, e.g., sterile water, solutions containing inorganic salts, or cationic surface active agents including sodium chloride, saline, e.g., phosphate buffered saline, potassium chloride, sodium sulfate, potassium sulfate, EDTA, ammonium sulfate, ammonium acetate, and sodium acetate. A specific example of a mixing solution is 0.9% NaCl saline solution (available from Baxter).

The concentration of mixing solution in the substitute composition varies and can be a function of, for example, the source (e.g., tissue bank) of the demineralized bone matrix, and/or the desired consistency of the composition. Also, the amount of mixing solution added to the mixture of powders can affect the time the composition takes to set, i.e., the set time. Increasing the amount of mixing solution can increase the set time, and decreasing the amount of mixing solution added to the mixture of powders can reduce the set time. For example, for a putty having HPMC, 2.6 grams of water provided a set time of about 10-15 minutes, while 4.0 grams of water provided a set time of about 60 minutes.

In some embodiments, for 100 parts of calcium sulfate (e.g., $CaSO_4 \cdot \frac{1}{2}H_2O$), the composition includes between about 40 and about 60 parts of the mixing solution, such as between about 45 and about 55 parts, or between about 49 and about 51 parts, or about 50 parts. The composition may include greater than or equal to about 40, 45, 50, or 55 parts of the mixing solution; and/or less than or equal to about 60, 55, 50, or 45 parts of the mixing solution. Mixtures of two or more mixing solutions can be used.

The mixing solution can further include one or more additives such as, for example, bone marrow aspirate, platelet concentrate, blood, pharmaceutical additives in solution, or combinations of these materials. Other examples of additives include medicaments or pesticides. Examples of medicaments are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cis-platinum, ifosfamide, methotrexate, and doxorubicin hydrochloride (Adriamycin®). Examples of growth factors are transforming growth factor beta (TGF-Beta), bone morphogenic protein (BMP), basic fibroblast growth factor, platelet-derived growth factor, and other polypeptide growth factors. Examples of analgesics are anesthetics such as lidocaine hydrochloride (Xylocaine®), bipivacaine hydrochloride (Marcaine®), and non-steroidal anti-inflammatory drugs such as ketorolac tromethamine (Toradol®) Certain mixing solution and/or additives can affect, e.g., delay, the hardening properties of the composition. The additive(s) can be added to the composition after the demineralized bone matrix has been added.

The composition as formed can be a conforming material having a paste-like or putty-like consistency, e.g., like Plaster of Paris, that can be applied digitally. The composition can be injected into a target site, for example, to fill into cracks or voids. In some embodiments, the composition is capable of setting to a hardness, e.g., about 4.3 MPa, in about 5-15 minutes, e.g., greater than 5, 7, 9, 11, or 13 minutes, and/or less than 15, 13, 11, 9, or 7 minutes.

The hardened composition can be used for intra-operative support of hardware, such as orthopedic hardware, e.g., bone plates, distal radius hardware, and hardware used for tibial plateau fractures.

The following example is illustrative and not intended to be limiting.

EXAMPLE

A mixture of surgical-grade calcium sulfate hemihydrate (SGCSH) and hydroxypropylmethylcellulose (5.0 g total, 4.9 g hemihydrate with 0.1 g HPMC) was mixed and bottled. In a separate bottle, 0.96 g DBM was packaged. In a third vial, 2.38 g water was packaged. All three bottles were electron beam sterilized at 18-26 kGy. To mix the putty, the SGCSH blend was emptied into a bowl and the water was added. The powder was mixed for approximately 30 seconds and then allowed to rest for 30 seconds. After one minute had passed since the water had been added to the hemihydrate powder, the DBM was added to the calcium sulfate mixture and mixed thoroughly for approximately 30 seconds. A putty like material was formed, setting in approximately 7 minutes. The strength of the hardened putty was approximately 4 MPa.

OTHER EMBODIMENTS

In some embodiments, the composition further includes a bioactive agent. Examples of bioactive agents include growth factors, hyaluronic acid, bone morphogenic proteins, bone autograft, and bone marrow, etc. The composition may include sodium bicarbonate. For example, the composition may include 0.1-2% sodium bicarbonate by weight to provide a porous structure in the resultant composition.

Alternatively or in addition, the bone graft substitute composition may include one or more additives such as an antiviral agent, an antimicrobial agent, an antibiotic agent, an amino acid, a peptide, a vitamin, an inorganic element, a protein synthesis co-factor, a hormone, an endocrine tissue, a synthesizer, an enzyme, a polymer cell scaffolding agent with parenchymal cells, an angiogenic drug, a collagen lattice, an antigenic agent, a cytoskeletal agent, mesenchymal stem cells, a bone digester, an antitumor agent, an cellular attractant, fibronectin, a growth hormone, a cellular attachment agent, an immunosuppressant, a nucleic acid, a surface active agent, synthetically derived or naturally derived chips of minerals such as calcium phosphate, e.g., hydroxyapatite or tricalcium phosphate, or calcium carbonate, a penetration enhancer, allografts, e.g., a bone allograft, cancellous bone chip (an osteoconductive substrate), and chunks, shards, and/or pellets of calcium sulfate.

A number of embodiments of the invention have been described. Nevertheless, it will be understood that various modifications may be made without departing from the spirit and scope of the invention.

What is claimed is:

1. A method of making a bone graft substitute composition, comprising the following steps:
    a) mixing calcium sulfate hemihydrate, a plasticizing material, and an aqueous mixing solution for a time sufficient to form a blend;
    b) waiting a predetermined period of time after forming the blend, wherein said predetermined period of time is at least about 30 seconds; and then
    c) mixing the blend and a demineralized bone material to produce the bone graft substitute composition.

2. The method of claim 1, wherein the blend is continuously mixed during the step b).

3. The method of claim 1, wherein said mixing of step a) comprises mixing for at least about 30 seconds to form the blend.

4. The method of claim 1, wherein the steps a) and b) have a combined time of at least about one minute.

5. The method of claim 1, wherein the blend further comprises an accelerant that accelerates formation of calcium sulfide dihydrate from the calcium sulfate hemihydrate.

6. The method of claim 5, wherein the accelerant is selected from the group consisting of calcium sulfate dihydrate, potassium sulfate, sodium sulfate, and mixtures thereof.

7. The method of claim 5, wherein the accelerant is calcium sulfide dihydrate coated with sucrose.

8. The method of claim 1, wherein the plasticizing material is selected from the group consisting of cellulose derivatives, glycerol, vinyl alcohols, stearic acid, hyaluronic acid, and mixtures thereof.

9. The method of claim 1, wherein the plasticizing material is selected from the group consisting of sodium carboxymethylcellulose, methylcellulose, hydroxypropylmethylcellulose, hydroxypropylcellulose, ethylcellulose, hydroxyethylcellulose, cellulose acetate butyrate, and mixtures thereof.

10. The method of claim 1, wherein the aqueous mixing solution comprises sterile water, or sterile water comprising inorganic salts, cationic surface active agents, or combinations thereof.

11. The method of claim 1, further comprising mixing an additive into the blend or the mixture of the blend and the demineralized bone material, the additive being selected from the group consisting of bone marrow aspirate, platelet concentrate, blood, medicaments, pesticides, sodium bicarbonate, growth factors, bone morphogenic proteins, bone autograft, calcium phosphates, calcium carbonate, and mixtures thereof.

12. The method of claim 1, wherein the bone graft substitute composition has the consistency of a paste or putty, and can be applied to the site of a bone defect digitally or by injection.

13. method of claim 1, wherein the demineralized bone material is in freeze-dried form and has a particle size of about 125 to about 850 microns.

14. The method of claim 1, wherein the bone graft substitute composition comprises:
    100 parts of calcium sulfate hemihydrate;
    about 0.5 to about 5 parts of the plasticizing material; and
    about 10 to about 30 parts of demineralized bone.

15. The method of claim 5, wherein the bone graft substitute composition comprises:
    100 parts of calcium sulfate hemihydrate;
    about 0.5 to about 5 parts of accelerant that accelerates formation of calcium sulfate dihydrate from the calcium sulfate hemihydrate;
    about 0.5 to about 5 parts of plasticizing material; and
    about 10 to about 30 parts of demineralized bone.

16. A kit for forming a bone graft substitute composition, comprising:
    a) a dry powder mixture of calcium sulfate hemihydrate and a plasticizing material;
    b) aqueous mixing solution;
    c) a demineralized bone material in particulate form;
    wherein a), b) and c) are separately packaged; and
    d) a set of instructions directing a kit user to perform the method of claim 1.

17. A method of making a bone graft substitute composition, comprising:
    a) mixing surgical grade calcium sulfate hemihydrate, a cellulose derivative, calcium sulfate dihydrate coated with sucrose, and an aqueous mixing solution for a time sufficient to form a blend;
    b) waiting a predetermined period of time after forming the blend, wherein said predetermined period of time is at least about thirty seconds; and then
    c) mixing the blend and a freeze-dried demineralized bone material to produce the bone graft substitute composition,
    wherein the bone graft substitute composition has the consistency of a paste or putty, and can be applied to the site of a bone defect digitally or by injection.

18. The method of claim 17, wherein the steps a) and b) have a combined time of at least about one minute.

19. A kit for forming a bone graft substitute composition, comprising, separately packaged:
    a) a dry powder mixture of calcium sulfate hemihydrite and a plasticizing material;
    b) an aqueous mixing solution; and
    c) a demineralized bone material in particulate form unblended with the dry powder mixture or the aqueous mixing solution.

20. The kit of claim 18, wherein the dry powder mixture further comprises an accelerant that accelerates formation of calcium sulfate dihydrate from the calcium sulfate hemihydrate.

21. The kit of claim 19, wherein the accelerant is calcium sulfide dihydrate coated with sucrose.

22. The kit of claim 18, wherein the plasticizing material is selected from the group consisting of cellulose derivatives, glycerol, vinyl alcohols, stearic acid, hyaluronic acid, and mixtures thereof.

23. The kit of claim 18, wherein the plasticizing material is selected from the group consisting of sodium carboxymethylcellulose, methylcellulase, hydroxypropylmethylcellulose, hydroxypropylcellulose, ethylcellulose, hydroxyethylccllulose, cellulose acetate butyrate, and mixtures thereof.

24. The kit of claim 18, wherein the demineralized bone material is in freeze-dried form and has a particle size of about 125 to about 850 microns.

* * * * *

UNITED STATES PATENT AND TRADEMARK OFFICE
CERTIFICATE OF CORRECTION

PATENT NO. : 7,658,768 B2 Page 1 of 1
APPLICATION NO. : 11/872564
DATED : February 9, 2010
INVENTOR(S) : Leasa C. Miller et al.

It is certified that error appears in the above-identified patent and that said Letters Patent is hereby corrected as shown below:

Title Page 1, in the (73) Assignee section, please amend Arlington, [[TX]] to Arlington, TN.

In Claim 19, column 6, line 52, please change hemihydrite to hemihydrates.

In Claim 20, column 6, line 58, please change claim [[18]] to claim 19.

In Claim 21, column 6, line 62, please change claim [[19]] to claim 20.

In Claim 22, column 6, line 64, please change claim [[18]] to claim 19.

In Claim 23, column 7, line 1, please change claim [[18]] to claim 19.

In Claim 24, column 8, line 1, please change claim [[18]] to claim 19.

Signed and Sealed this

Twenty-fourth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,658,768 B2 | Page 1 of 1 |
| APPLICATION NO. | : 11/872564 | |
| DATED | : February 9, 2010 | |
| INVENTOR(S) | : Leasa C. Miller et al. | |

It is certified that error appears in the above-identified patent and that said Letters Patent is hereby corrected as shown below:

Title Page 1, in the (73) Assignee section, please amend Arlington, [[TX]] to Arlington, TN.

In Claim 19, column 6, line 52, please change hemihydrite to hemihydrate.

In Claim 20, column 6, line 58, please change claim [[18]] to claim 19.

In Claim 21, column 6, line 62, please change claim [[19]] to claim 20.

In Claim 22, column 6, line 64, please change claim [[18]] to claim 19.

In Claim 23, column 7, line 1, please change claim [[18]] to claim 19.

In Claim 24, column 8, line 1, please change claim [[18]] to claim 19.

This certificate supersedes the Certificate of Correction issued August 24, 2010.

Signed and Sealed this
Fourth Day of January, 2011

David J. Kappos
*Director of the United States Patent and Trademark Office*